United States Patent [19]

Crowe et al.

[11] 3,946,052

[45] Mar. 23, 1976

[54] 19-NORPREGNA-1,3,5(10)-TRIEN-3-OL AND LOWERALKYL HOMOLOGS THEREOF HAVING POSTCOITAL ANTIFERTILITY ACTIVITY

[75] Inventors: David F. Crowe; Richard H. Peters, both of San Jose; Masato Tanabe, Palo Alto; George Detre, San Jose, all of Calif.

[73] Assignee: Stanford Research Institute, Menlo Park, Calif.

[22] Filed: June 16, 1975

[21] Appl. No.: 587,256

[52] U.S. Cl. ............ 260/397.5; 260/397.4; 424/238
[51] Int. Cl.² ............................................. C07J 1/00
[58] Field of Search .................. 260/397.5; 424/238

[56] References Cited
OTHER PUBLICATIONS

U.S. Department of HEW, National Institute of Health, Endocrine Bioassay Data, Uterotropic, Issue 3, June 1968, p. 113.

*Primary Examiner*—Elbert L. Roberts
*Attorney, Agent, or Firm*—Donovan J. De Witt

[57] ABSTRACT

19-Norpregna-1,3,5(10)-trien-3-ol and loweralkyl homologs thereof wherein the alkyl group attached in the 17β position contains from 2 to 7 carbon atoms. Said compounds, along with the corresponding known 17β-methyl derivative, are found to have antifertility activity, and particularly postcoital antifertility activity, along with very low estrogenic activity, when administered orally to mammals.

6 Claims, No Drawings

19-NORPREGNA-1,3,5(10)-TRIEN-3-OL AND LOWERALKYL HOMOLOGS THEREOF HAVING POSTCOITAL ANTIFERTILITY ACTIVITY

BACKGROUND OF INVENTION

The compound 17β-methyl-estra-1,3,5(10)-trien-3-ol is disclosed in U.S. Department of Health, Education, and Welfare, National Institute of Health, Endocrine Bioassay Data, Uterotropic, Issue 3, June 1968, p. 113, Entry Nos. 4324–5962, compound NSC 52244, where it is proposed for use as an anticancer agent.

SUMMARY OF THE INVENTION

The present invention rests in part on the discovery of novel steroid compounds having the structure

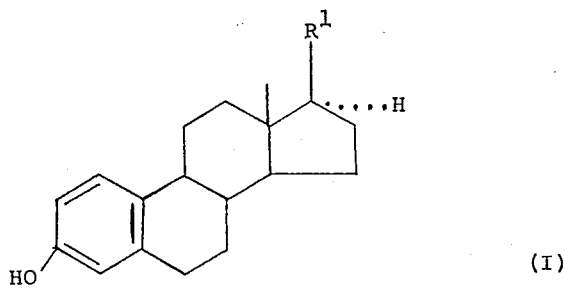

(I)

In said structure the $R^1$ group attached at the 17β position of the molecule represents a straight or branched chain loweralkyl group of from 2 to 7 carbon atoms. Representative loweralkyl groups falling into this class include ethyl, n-propyl, isopropyl, n-butyl, isobutyl, sec-butyl and tert-butyl and the various pentyl, hexyl or heptyl groups of straight or branched chain configuration. Invention also lies in the discovery that the aforesaid novel compounds as well as the known compound 17β-methyl-estra-1,3,5-(10)-trien-3-ol have antifertility activity, and more particularly postcoital antifertility activity, when orally administered to mammals. As said compounds are orally administered it is found that for a given level for antifertility activity the accompanying estrogenic activity is greatly reduced as measured against ethynylestradiol as a reference. For example, in the case of 19-norpregna-1,3,5(10)-trien-3-ol which forms the subject of Example 1 hereof, there is obtained a remarkable 100-fold separation of postcoital antifertility activity from estrogenic activity, this separation factor being based on a comparison with the results obtained using approximately like amounts of ethynylestradiol wherein each of the postcoital antifertility and estrogenic activity factors has a value of 1.

The novel steroid compounds of the present invention are white powdery materials having well-defined melting points. They are water-insoluble, slightly soluble in methanol and have good solubility in chloroform and various other organic solvents. They can be prepared by the catalyzed hydrogenation of the corresponding 1,3,5(10),17(20)-tetraen-3-ol precursor compounds. This reaction proceeds readily under ambient conditions of temperature and pressure in the presense of a catalyst such as supported palladium and a solvent such as ethyl acetate, for example. On filtering off the product and removing the ethyl acetate under reduced pressure, the desired beta isomer compound can be obtained by recrystallization using a solvent such as hexane, for example. Methods for preparing the tetraene precursor compounds are provided in the examples.

The following examples illustrate the invention in various of its embodiments.

EXAMPLE 1

19-Norpregna-1,3,5(10)-trien-3-ol

Preparation of 19-norpregna-1,3,5(10),17(20)-tetraen-3-ol from estrone and ethyltriphenyl phosphonium bromide:

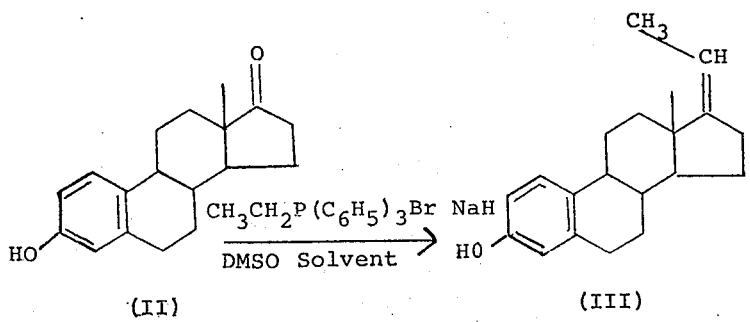

A suspension of 9.6 g of sodium hydride (50% dispersion in mineral oil which is washed with hexane and dried at reduced pressure) in 150 ml of dimethylsulfoxide is heated to 70°–75°C for 1 hour resulting in a light green solution. After cooling, a solution of 74.4 g of ethyltriphenyl phosphonium bromide in 300 ml of dimethylsulfoxide is added to produce a deep red solution. To this solution is added 9.5 g of estrone in 300 ml of dimethylsulfoxide. After heating the reaction mixture at 60°C for 18 hours, the reaction mixture is poured into ice water and extracted with ether. The ether solution is washed with water, dried over sodium sulfate and evaporated at reduced pressure to yield 16.9 g of a crude gum. The resulting gum is dissolved in 1.0 l of a petroleum ether (30°–60°C)-ethyl acetate mixture (1:1) and filtered through 400 g of silica gel. The white solid collected after evaporation is purified by dry column chromatography on 1.0 Kg of Woelm silica gel for dry column chromatography. The column is developed with a chloroform — 5% ethyl acetate mixture. The column is cut and the silica gel eluted with ethyl acetate. After evaporation of the ethyl acetate, there is obtained 6.8 g of 19-norpregna-1,3,5(10),17(20)-tetraen-3-ol. An analytical sample obtained by recrystallization from methanol has a melting point of 133°–136°C. (Lit. 137°–139°C, A. M. Krubiner and E. P. Oliveto, J. Org. Chem. 31, 24 (1966).
Preparation of 19-norpregna-1,3,5(10)-trien-3-ol from 19-norpregna-1,3,5(10),17(20)-tetraen-3-ol tained by the reaction of estrone with n-butyltriphenyl phosphonium bromide). The resulting crystalline product, identified as the captioned compound by NMR and IR analysis, has a melting point of 98°–100°C and $[\alpha]_D$ + 81. It is found to have a molecular weight of 312.

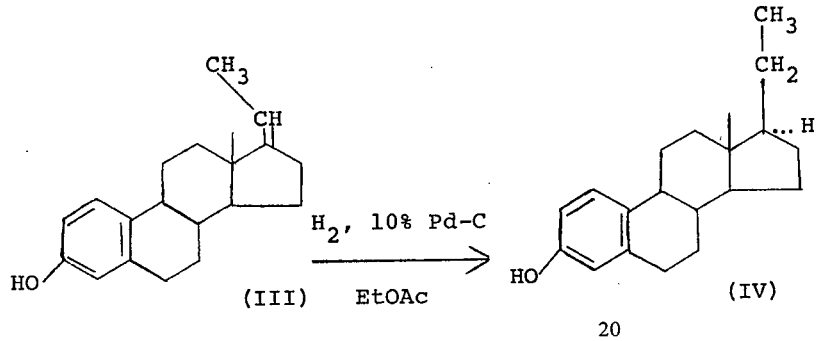

A solution of 500 mg of 19-norpregna-1,3,5(10),17-(20)-tetraen-3-ol in 20.0 ml ethyl acetate containing 25 mg of 10% palladium on carbon catalyst is hydrogenated at room temperature and atmospheric pressure. The resulting suspension is filtered through celite and the ethyl acetate removed at reduced pressure. Recrystallization from hexane afford 400 mg of 19-norpregna-1,3,5(10)-trien-3-ol, melting point 106°–108°C, $[\alpha]_D$ + 86 (CH$_3$OH). Analysis calculated for C$_{20}$H$_{28}$O: C, 84.45, H, 9.92. Found: C, 84.28; H, 9.89.

EXAMPLE 2

17β-Methyl-estra-1,3,5(10)-trien-3-ol

This operation is conducted in accordance with the general procedures given in Example 1 except that as the steroid reactant there is employed 17-methylene-estra-1,3,5(10)-tetraen-3-ol (obtained by the reaction of estrone with methyltriphenyl phosphonium bromide) and the crystalline product is obtained by recrystallization from methanol. This product, which is identified as the captioned compound by NMR and IR analysis, is found to have a melting point of 133°–135°C and a $[\alpha]_D$ + 88 (CH$_3$OH). It is found to contain 79.34% carbon and 9.70% hydrogen as against theoretical values (assuming a product containing one mole of methanol) of 79.42% and 10.00% for these elements.

EXAMPLE 3

21-Methyl-19-norpregna-1,3,5(10)-trien-3-ol

This operation is conducted in accordance with the general procedure of Example 1 except that the steroid reactant is 21-methyl-19-norpregna-1,3,5(10),17(20)-tetraen-3-ol (obtained by reaction of estrone with n-propyltriphenyl phosphonium bromide) and the final product is obtained by recrystallization from hexane. The white crystalline product so obtained, which is identified as the captioned compound by NMR and IR method of analysis, has a melting point of 129°–130°C and $[\alpha]_D$ + 92 (CH$_3$OH). It is found to contain 84.46% carbon and 9.99% hydrogen as against theoretical values of 84.51% and 10.13% for these elements.

EXAMPLE 4

21-Ethyl-19-norpregna-1,3,5(10)-trien-3-ol

This operation is conducted in accordance with the general procedure given above in Example 1 except that as the starting compound there is employed 21-ethyl-19-norpregna-1,3,5(10),17(20)-tetraen-3-ol (ob-

EXAMPLES 5 to 13

In accordance with the general methods of preparation recited in Example 1 above the following reactions are conducted to obtain the indicated product compounds, the starting material in each case being obtained by the reaction of estrone with the appropriate alkyltriphenyl phosphonium bromide:

21-n-Propyl-19-norpregna-1,3,5(10)-trien-3-ol, molecular weight of 326, prepared from 21-n-propyl-19-norpregna-1,3,5(10),17(20)-tetraen-3-ol. 21-n-Butyl-19-norpregna-1,3,5(10)-trien-3-ol, molecular weight 340, prepared from 21-n-butyl-19-norpregna-1,3,5(10),17(20)-tetraen-3-ol.

21-n-Pentyl-19-norpregna-1,3,5(10)-trien-3-ol, molecular weight 354, prepared from 21-n-pentyl-19-norpregna-1,3,5(10),17(20)-tetraen-3-ol.

20-Methyl-19-norpregna-1,3,5(10)-trien-3-ol, molecular weight 298, prepared from 20-methyl-19-norpregna-1,3,5(10),17(20)-tetraen-3-ol.

20-Ethyl-19-norpregna-1,3,5(10)-trien-3-ol, molecular weight 312, prepared from 20-ethyl-19-norpregna-1,3,5(10),17(20)-tetraen-3-ol.

20-n-Propyl-19-norpregna-1,3,5(10)-trien-3-ol, molecular weight 326, prepared from 20-n-propyl-19-norpregna-1,3,5(10),17(20)-tetraen-3-ol.

20-n-Butyl-19-norpregna-1,3,5(10)-trien-3-ol, molecular weight 340, prepared from 20-n-butyl-19-norpregna-1,3,5(10),17(20)-tetraen-3-ol.

20-n-Pentyl-19-norpregna-1,3,5(10)-trien-3-ol, molecular weight 354, prepared from 20-n-pentyl-19-norpregna-1,3,5(10),17(20)-tetraen-3-ol.

20-Isopropyl-19-norpregna-1,3,5(10)-trien-3-ol, molecular weight 326, prepared from 20-isopropyl-19-norpregna-1,3,5(10),17(20)-tetraen-3-ol.

All of the compounds of this invention have good postcoital antifertility activity and very low estrogenic activity. The preferred compound for use in mammals to control fertility is 19-norpregna-1,3,5(10)-trien-3-ol, and results obtained on orally administering this compound to female rats are presented below. This diminished estrogenic activity, observed on administering the compounds of the present invention at dosage levels giving complete protection against pregnancy, is a highly desirable quality since thromboembolism and other clinically observed undesirable side effects associated with higher levels of estrogenic activity are thus minimized or avoided altogether.

While good results can be obtained by orally administering novel compounds of this invention, as well as 17β-methyl-estra-1,3,5(10)-trien-3-ol, other forms of administration can produce equally good results. Thus, all of said compounds can be prepared and administered to mammals, birds and other animals, in a wide variety of oral or parenteral dosage forms, singly or in admixture with other coacting compounds. They can be administered with a pharmaceutical carrier which can be a solid material or a liquid in which the compound is dissolved, dispersed or suspended. The solid compositions can take the form of tablets, powders, capsules, pills, or the like, preferably in unit dosage forms for simple administration or precise dosages. The liquid compositions can take the form of solutions, emulsions, suspensions, syrups, or elixirs.

EXAMPLE 14

Tests were made to determine the oral postcoital antifertility activity of 19-norpregna-1,3,5(10)-trien-3-ol. In this test adult cycling female rats, obtained from the Holtzman Rat Company, were selected in the proestrous phase of the cycle. Each female was caged overnight with two adult males. The finding of sperm in the vaginal smear the following morning was used as evidence of insemination. Treatment began on the day of finding sperm and continued for a total of 7 days. The rats were sacrificed on day 8 of pregnancy, and the number of implantation sites, resorbing embryos, empty sites, and corpora lutea were recorded for each female. The results obtained were as follows:

| Compound | No. of Animals | Daily Dose (μg/kg) | No. of Animals with Implants | Total No. of Normal Fetuses | Total No. of Resorbing Fetuses | Animals Pregnant (%) |
|---|---|---|---|---|---|---|
| Control | 5 | — | 5 | 60 | 0 | 100 |
| Test Compound | 5 | 1000 | 0 | 0 | 0 | 0 |

Diluent
CMC = Carbomethoxy cellusolve

EXAMPLE 15

Tests were made to determine the oral postcoital antifertility activity of 19-norpregna-1,3,5(10)-trien-3-ol at lower treatment levels then employed in the previous example. In this test adult female Sprague-Dawley rats were allowed to cohabit with proven fertile males. Vaginal smears were taken every morning, and females having sperm in the vagina were removed for treatment. The day sperm was found was considered day zero of pregnancy. Animals were treated orally on days 0 through 6. Autopsy was performed on day 7 of pregnancy. The presence and number of normal and resorbing fetuses were determined. The results obtained are as follows:

| Compound | No. of Animals | (μg/kg/day) | No. of Animals with Implants | Total No. of Normal Fetuses | Total No. of Resorbing Fetuses | Animals Pregnant (%) |
|---|---|---|---|---|---|---|
| Control | 5 | CMC | 5 | 58 | 0 | 100 |
| Test Compound | 5 | 100 | 3 | 40 | 2 | 60 |
|  | 5 | 250 | 0 | 0 | 0 | 0 |

Diluent:
CMC = Carbomethoxy cellusolve

EXAMPLE 16

Tests were made to determine the oral estrogenic activity of 19-norpregna-1,3,5(10)-trien-3-ol. In this test immature female Sprague-Dawley rats were orally administered the compound for 3 days. Animals were autopsied on the day following the last treatment. Uteri were excised, cleaned, and weighed on a torsion balance to the nearest 0.2 mg. The results obtained were as follows:

| Treatment, Total Dose (μg) | Number of Animals | Average Body Weight (g) | | Average Uterine Weight ± S.E. (mg) |
|---|---|---|---|---|
| | | Initial | Final | |
| Control CMC | 10 | 40.3 | 52.4 | 24.9 ± 1.56 |
| Test Compound | | | | |
| 25 | 10 | 41.3 | 54.3 | 43.9 ± 0.72 |
| 50 | 10 | 39.7 | 55.1 | 56.2 ± 1.52 |
| 100 | 9 | 40.9 | 54.1 | 70.7 ± 2.44 |

Diluent:
CMC = carbomethoxy cellusolve

In other operations conducted to determine the oral estrogenic activity of ethynylestradiol (EE) it was found that the average uterine weight was somewhat larger than any of the uterine weights expressed above in Example 16 even when the EE compound was administered at total dosage levels as low as 1.11 μg. This shows that 19-norpregna-1,3,5(10)-trien-3-ol has achieved a remarkable 100-fold separation of postcoital antifertility activity from estrogenic activity as compared with the EE compound. Complete protection against pregnancy in rats is obtained with EE in oral postcoital treatments at approximately the same levels, e.g., 200 μg/kg/day, as prevail when using 19-norpregna-1,3,5(10)-trien-3-ol.

As indicated above, the compounds of this invention, as embraced within Formula I as well as 17β-methyl-estra-1,3,5(10)-trien-3-ol, are useful for their antifertility activity in mammals, including man. A determination of the effective postcoitally administered dosage required to prevent pregnancy depends on the particular compound involved, route of administration, the mammalian species involved and the individual's response thereto. In general, a dose of between about 0.01 mg to about 5 mgs of any one of these compounds administered, e.g., orally, once a day is effective to achieve the desired result of pregnancy prevention.

We claim that:

1. A compound having the structure

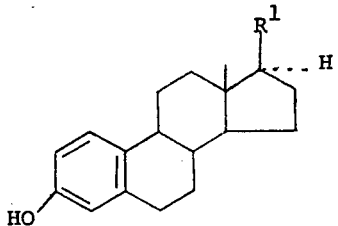

wherein R¹ represents a straight or branched loweralkyl group of from 2 to 7 carbon atoms.

2. The compound of claim 1 which is 19-norpregna-1,3,5(10)-trien-3-ol.

3. The compound of claim 1 which is 21-methyl-19-norpregna-1,3,5(10)-trien-3-ol.

4. The compound of claim 1 which is 21-ethyl-19-norpregna-1,3,5(10)-trien-3-ol.

5. A method of preventing pregnancy in mammals which comprises postcoitally administering to said mammals an effective amount of a compound of the structure

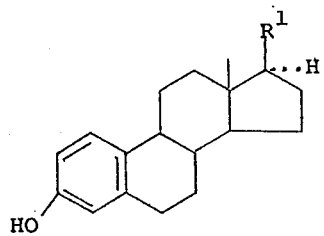

wherein R¹ represents a straight or branched loweralkyl group of from 2 to 7 carbon atoms.

6. A method of preventing pregnancy in mammals which comprises postcoitally administering to said mammals an effective amount of 17β-methyl-estra-1,3,5,(10)-trien-3-ol.

* * * * *